US010134127B2

(12) United States Patent
Falahatpisheh et al.

(10) Patent No.: US 10,134,127 B2
(45) Date of Patent: Nov. 20, 2018

(54) METHOD FOR POST-PROCESSING FLOW-SENSITIVE PHASE CONTRAST MAGNETIC RESONANCE IMAGES (71) Applicant: The Regents of the University of California, Oakland, CA (US)

(72) Inventors: Ahmad Falahatpisheh, Irvine, CA (US); Arash Kheradvar, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 17 days.

(21) Appl. No.: 15/102,853

(22) PCT Filed: Dec. 10, 2014

(86) PCT No.: PCT/US2014/069603
§ 371 (c)(1),
(2) Date: Jun. 8, 2016

(87) PCT Pub. No.: WO2015/089222
PCT Pub. Date: Jun. 18, 2015

(65) Prior Publication Data
US 2016/0358328 A1 Dec. 8, 2016

Related U.S. Application Data (60) Provisional application No. 61/915,275, filed on Dec. 12, 2013, provisional application No. 62/049,270, filed on Sep. 11, 2014.

(51) Int. Cl.
*G06K 9/00* (2006.01)
*G06T 7/00* (2017.01)
(Continued)

(52) U.S. Cl.
CPC ........ *G06T 7/0012* (2013.01); *G01R 33/5608* (2013.01); *G01R 33/56316* (2013.01);
(Continued)

(58) Field of Classification Search
None
See application file for complete search history.

(56) References Cited

U.S. PATENT DOCUMENTS 5,354,017 A 10/1994 Levich
6,443,010 B1 * 9/2002 Scofield ................. G01N 29/14
73/587

(Continued)

OTHER PUBLICATIONS

Ebbers, T., Wigström, L., Bolger, A. F., Engvall, J., & Karlsson, M. (2001). Estimation of relative cardiovascular pressures using time-resolved three-dimensional phase contrast MRI. Magnetic resonance in medicine, 45(5), 872-879.*

(Continued)

*Primary Examiner* — Vu Le
*Assistant Examiner* — Samah Beg
(74) *Attorney, Agent, or Firm* — Knobbe, Martens Olson & Bear, LLP (57) ABSTRACT A method for generating fluid flow images of a region of interest is disclosed. The method includes: scanning the region of interest to acquire a set of 4D-Flow magnetic resonance images, wherein the set comprises an anatomical magnitude image, a first velocity component image, a second velocity component image, and a third velocity component image; isolating the anatomical magnitude image, the first velocity component image, the second velocity component image, and the third velocity component image from the set of 4D-Flow magnetic resonance images; converting the first, second, and third velocity component images into a velocity vector field; modeling a location of an anatomical wall within the region of interest; calculating at (Continued)

least one flow dynamics parameter for the region of interest; and generating a visual representation of the anatomical wall and the at least one flow dynamics parameter.

16 Claims, 9 Drawing Sheets

(51) Int. Cl.
*G06T 19/00* (2011.01)
*G01R 33/56* (2006.01)
*G01R 33/563* (2006.01)
*G06T 15/08* (2011.01)
*G06T 7/11* (2017.01)
*G06F 19/00* (2018.01)

(52) U.S. Cl.
CPC ............... *G06T 7/11* (2017.01); *G06T 15/08* (2013.01); *G06T 19/00* (2013.01); *G06F 19/321* (2013.01); *G06T 2210/24* (2013.01); *G06T 2210/41* (2013.01)

(56) References Cited

U.S. PATENT DOCUMENTS

| | | | |
|---|---|---|---|
| 8,532,358 B2 | 9/2013 | Kiraly | |
| 2009/0223309 A1* | 9/2009 | Kurz | G01F 1/46 73/863.03 |
| 2010/0002925 A1* | 1/2010 | Kiraly | G06K 9/342 382/131 |
| 2012/0253769 A1* | 10/2012 | Poondru | G06F 17/5009 703/9 |
| 2012/0265075 A1* | 10/2012 | Pedrizzetti | A61B 8/06 600/454 |
| 2013/0053658 A1* | 2/2013 | Peacock | A61B 5/055 600/309 |
| 2014/0149055 A1* | 5/2014 | Falahatpisheh | G01P 5/001 702/45 |
| 2016/0135775 A1* | 5/2016 | Mistretta | A61B 6/5247 600/411 |
| 2016/0140730 A1* | 5/2016 | Falahatpisheh | G01S 15/8984 382/131 |
| 2017/0098302 A1* | 4/2017 | Peters | G06T 7/0012 |
| 2017/0206291 A1* | 7/2017 | Abramov | G06F 17/5009 |

OTHER PUBLICATIONS

Nett, E. R. L., García-Rodríguez, S., Roldan, A., Wieben, O., & Johnson, K. (2013). Pressure difference measurements in stenotic flow phantom: comparison of 4D flow MRI, computational fluid dynamics, and pressure wire measurements. Proceedings of the international society for magnetic resonance in medicine, Salt Lake City, USA.*

Munson, Bruce R., et al. "Restrictions on Use of the Bernoulli Equation." Fundamentals of Fluid Mechanics, John Wiley & Sons, Inc., 2009, pp. 126-131.*

Petersson, S., "Fast and Accurate 4D Flow MRI for Cardiovascular Blood Flow Assessment," Linkopin University Medical Dissertation, Nov. 2013.

Jiang, J. et al. "Flow characteristics in a canine aneurysm model: A comparison of 4D accelerated phase-contrast MR measurements and computational fluid dynamics simulations," Journal of Medical Physics, vol. 38, Issue 11. Oct. 31, 2011.

International Search Report and Written Opinion dated Mar. 24, 2015 for PCT/US14/69603.

* cited by examiner

METHOD FOR POST-PROCESSING FLOW-SENSITIVE PHASE CONTRAST MAGNETIC RESONANCE IMAGES

CROSS REFERENCE TO RELATED APPLICATIONS

This application is the U.S. National Phase of International Application No. PCT/US2014/069603, filed Dec. 10, 2014, designating the U.S. and published in English as WO 2015/089222 on Jun. 18, 2015 which claims the benefit of U.S. Provisional Patent Application Nos. 61/915,275 filed Dec. 12, 2013 and 62/049,270 filed Sep. 11, 2014. Any and all applications for which a foreign or domestic priority claim is identified here or in the Application Data Sheet as filed with the present application are hereby incorporated by reference under 37 CFR 1.57.

BACKGROUND

Field

Methods are described for reading and processing flow sensitive phase contrast magnetic resonance images to calculate and display dynamic flow parameters in a region of interest.

Description of the Related Art

Magnetic Resonance Imaging ("MRI") refers to a medical imaging technique that utilizes strong magnetic fields to safely scan body tissues and generate two- and three-dimensional images of those tissues. Through the precise application of magnetic fields and radio signals, an MRI scan produces a series of image "slices" corresponding to planar regions of a three-dimensional scanned region, such as a subject's brain or chest cavity. Subsequent image processing generates high contrast images of internal body structures and tissues. In this way, MRI images enable physicians and clinicians to differentiate between different soft tissues within the body, such as brain, muscle, and heart tissue, as well as tumors and other diseased tissues.

Although MRI techniques and devices have been in use for many years, more recent technological developments have led to new and enhanced MRI methods. For example, Magnetic Resonance Angiography ("MRA") is a modern technique that is capable of generating high contrast images of tissues that move over time, such as flowing blood. MRA techniques therefore enable physicians to visualize the anatomical structures of a subject's circulatory system, including the heart, arteries, and veins.

In some circumstances, relative movement of tissues within the scanning region, such as, for example, the swelling of an artery during cardiac systole, can have the effect of clouding the resulting MR image. One method to address this issue has been to inject a contrast agent into the subject's circulation to effectively highlight the moving tissues during an MRI scan of the subject. However, due to their chemical composition, injection of such contrast agents is undesirable. Phase contrast ("PC") MRI techniques have been developed to address this issue. PC MRI techniques are capable of quantifying fluid flow by encoding velocity information into the phase of an MRI signal. Modern PC techniques can encode three-dimensional ("3D") velocity data, along with signal intensity and temporal data, into a given MR image slice. In this way, PC MRI techniques account for the relative movement of soft tissues within the scanning region, and enhance the contrast of the resulting output image slices without the use of chemical agents.

SUMMARY

A method for processing flow sensitive data of a region of interest is disclosed. In one embodiment, the method comprises: scanning the region of interest to acquire at least one image; isolating each of the at least one image; and converting the at least one image into a velocity vector field.

In a variation, the at least one image is at least one set of 4D-Flow magnetic resonance images. The at least one set of 4D-Flow magnetic resonance images may include an anatomical magnitude image and at least one velocity component image. In one embodiment, the at least one set of 4D-Flow magnetic resonance images may include a first velocity component image, a second velocity component image, and a third velocity component image. In a variation, each of the first velocity component image, the second velocity component image, and the third velocity component image are converted into a respective first velocity vector field, a respective second velocity vector field, and a respective third velocity vector field.

In one embodiment, the method further comprises modeling a location of an anatomical wall within the region of interest. In another embodiment, the method further comprises generating a visual representation of the anatomical wall In another embodiment, the method further comprises displaying the visual representation of the anatomical wall. In another embodiment, the method further comprises calculating at least one flow dynamics parameter for the region of interest. In another embodiment, the method further comprises generating a visual representation of the at least one flow dynamics parameter. In another embodiment, the method further comprises displaying the visual representation of the anatomical wall.

In further variations, the at least one flow dynamics may include circulation, Reynold stresses and/or helicity.

In another embodiment, scanning may further comprise saving the data into PAR/REC format or DICOM format.

In another embodiment, the method further comprises selecting a region of interest using a graphic user interface.

In another embodiment, the anatomical magnitude image may correspond to the image of the at least one set of 4D-Flow magnetic resonance images having the minimum mean.

In another embodiment, a method is disclosed for generating fluid flow images of a region of interest. The method includes: scanning the region of interest to acquire at least one set of 4D-Flow magnetic resonance images, wherein each set comprises an anatomical magnitude image, a first velocity component image, a second velocity component image, and a third velocity component image; isolating the anatomical magnitude image, the first velocity component image, the second velocity component image, and the third velocity component image from the at least one set of 4D-Flow magnetic resonance images; converting the first, second, and third velocity component images into a velocity vector field; modeling a location of an anatomical wall within the region of interest; calculating at least one flow dynamics parameter for the region of interest; generating a visual representation of the anatomical wall and the at least one flow dynamics parameter; and displaying the visual representation.

In another embodiment, a method is disclosed for generating fluid flow images of a region of interest. The method includes: scanning a region of interest to acquire a plurality of 4D-Flow magnetic resonance image sets, wherein each image set comprises an anatomical magnitude image, a first velocity component image, a second velocity component image, and a third velocity component image; converting the first, second, and third velocity component images into a first, second, and third physical velocity data set for each of the plurality of 4D-Flow magnetic resonance image sets; modeling a location of an anatomical wall within the region of interest, wherein the location of the anatomical wall is based on the mathematical combination of the anatomical magnitude image and the first, second, and third physical velocity data sets for each of the plurality of 4D-Flow magnetic resonance image sets; calculating at least one flow dynamics parameter for the region of interest; and generating a visual representation of the anatomical wall and the at least one flow dynamics parameter; and displaying the visual representation.

DETAILED DESCRIPTION

Disclosed herein are various embodiments of systems and methods discussed primarily in the context of reading and processing flow sensitive phase contrast magnetic resonance images to calculate and display dynamic flow parameters in a region of interest. At the same time, it will be understood that the concepts and principles embodied in the various embodiments can also be used in other contexts and technical areas other than those disclosed.

Although MRI techniques and methods are capable of producing flow-sensitive, phase contrast image slices, the present disclosure is directed to novel post-acquisition processing methods that allow clinicians to analyze and visualize MRI data for purposes of diagnosis and treatment. Accordingly, in one aspect, a method is disclosed for processing MRI data to model 3D anatomical structures within a scanned region of a subject along with visual representations of fluid flow characteristics within and around those structures. Flow-sensitive, phased contrast image data are referred to as 4D-Flow MRI data. 4D-Flow MRI data can be acquired using MRA or PC MRI scans. The 4D-Flow MRI data contains four datasets consisting of anatomical magnitude and three velocity component image series. In one example, the 4D-Flow MRI data is then processed and may be automatically parsed into its magnitude and velocity components. The 4D-Flow MRI data can be used for any number of purposes. In some embodiments of the disclosed methods, the data may be used to model anatomical structures in the patient. In some embodiments of the disclosed methods, the data may be used to calculate information relating to the fluid flow field of the scanned region. In some embodiments of the disclosed methods, a visualization of that information is generated to assist a clinician in the diagnosis or treatment of the subject.

Figure 1:
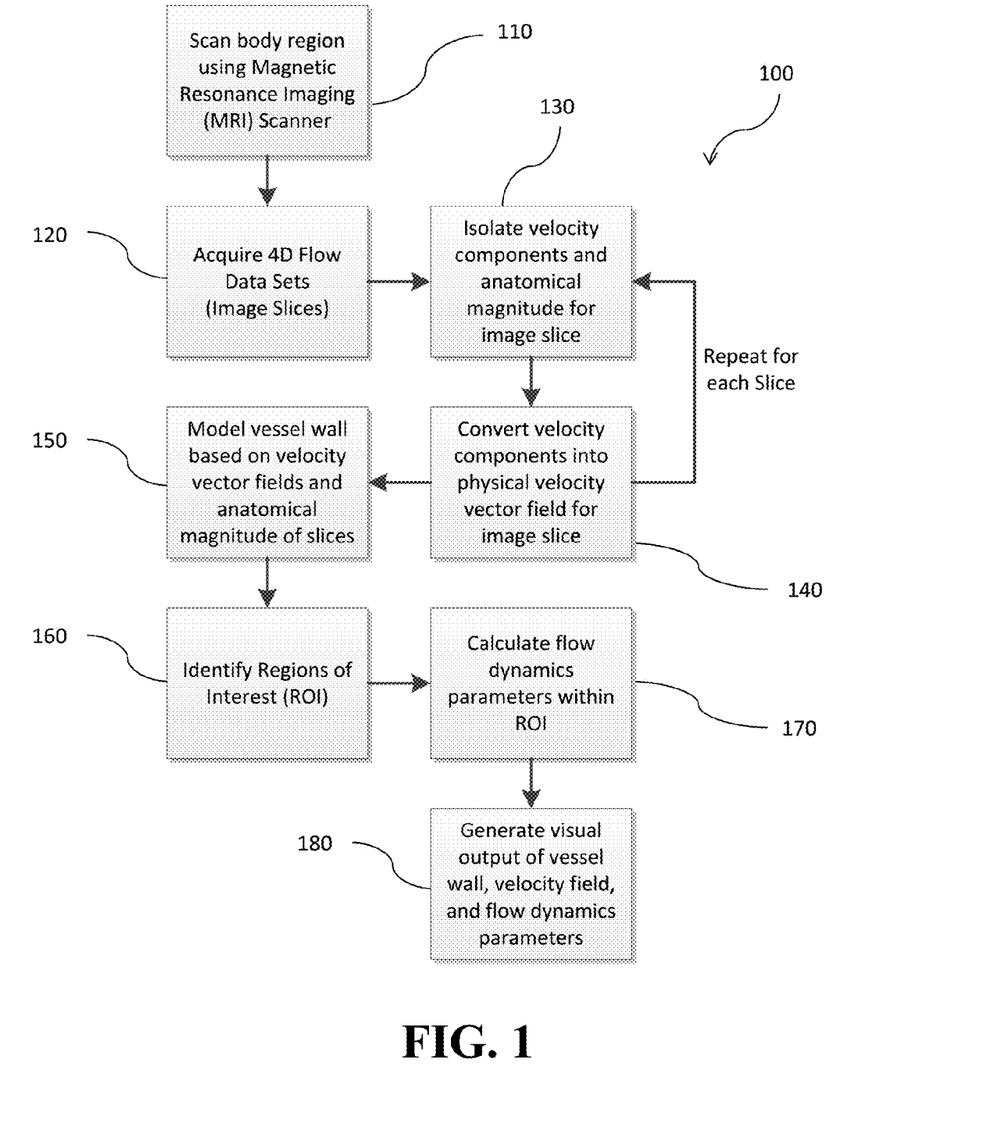
FIG. 1 illustrates a block diagram of an example of a method for post-processing flow-sensitive phase contrast magnetic resonance images.
Figure 2A:
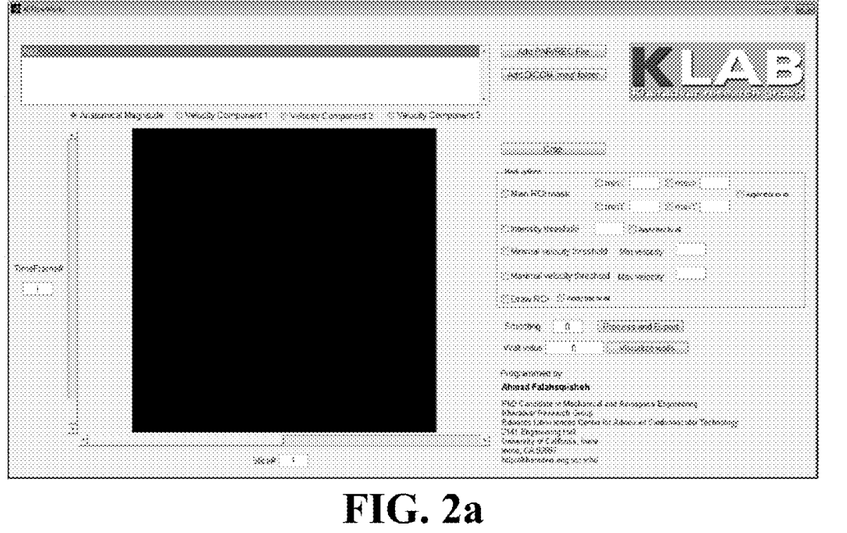
FIGS. 2a-b illustrate example screenshots of a graphical user interface depicting an anatomical magnitude image for a sample data set to be used in the method for post-processing flow-sensitive phase contrast magnetic resonance images.
Figure 2B:
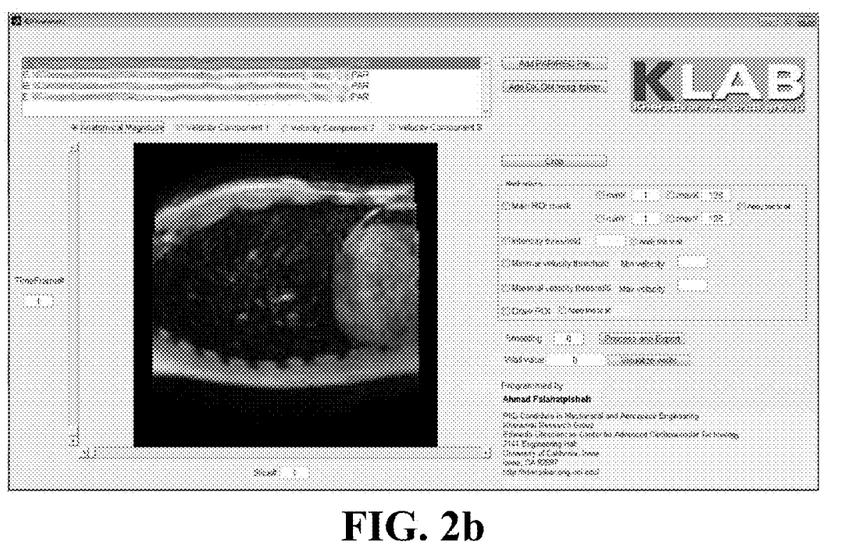
Figure 3A:
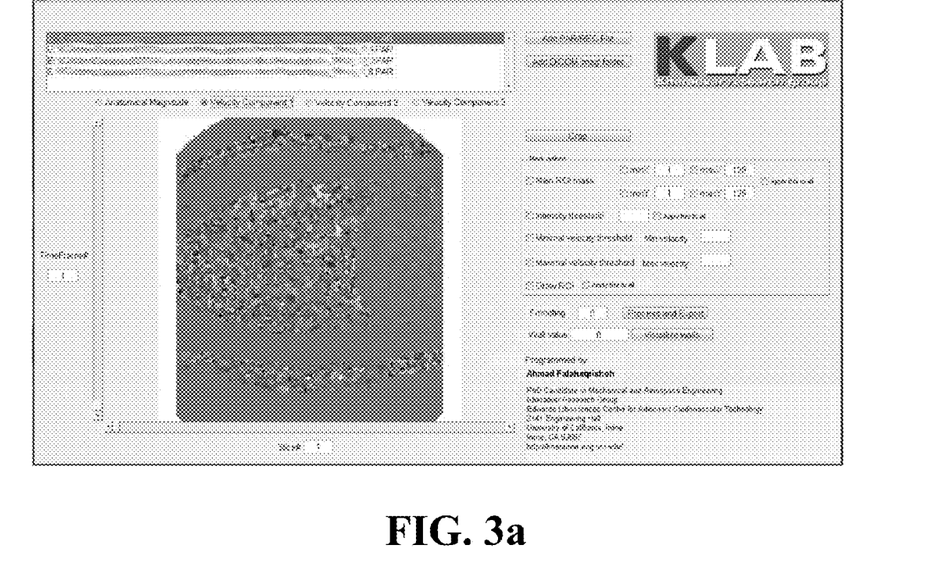
FIGS. 3a-b illustrate example screenshots of a graphical user interface depicting velocity components for a sample data set to be used in the method for post-processing flow-sensitive phase contrast magnetic resonance images.

FIG. 1 provides a flow chart of the method for post-processing flow-sensitive image data 100 according to an embodiment of the present method. Execution of the method, including image scanning and imputing of relevant parameters of the flow chart of the method for post-processing flow-sensitive image data 100 may be accomplished using a graphical user interface (GUI). An example of the GUI is shown in FIGS. 2a-2b and FIG. 3a. FIG. 2a shows an example of the main screen as the program is being loaded. FIGS. 2b and 3a show two example screens after a dataset is opened. FIG. 2b shows an example screen shot of an anatomical magnitude image. FIG. 3a shows an example screen shot of one of the velocity components. The details and process for obtaining each of the aforementioned images will be discussed in more detail below.

At step 110, the body is scanned using an MRI scanner. In one embodiment, the scanner used is a Philips scanner which saves data in Philips PAR/REC format (i.e. Philips data parameters (PAR) and Philips raw reconstructed data format (REC)). In another embodiment, the scanner used is a Siemens scanner which saves data in standard medical image protocol, known as DICOM.

Figure 3B:
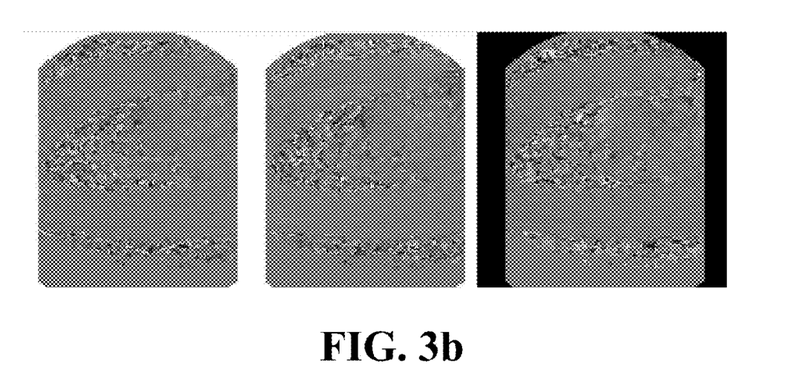
Figure 4:
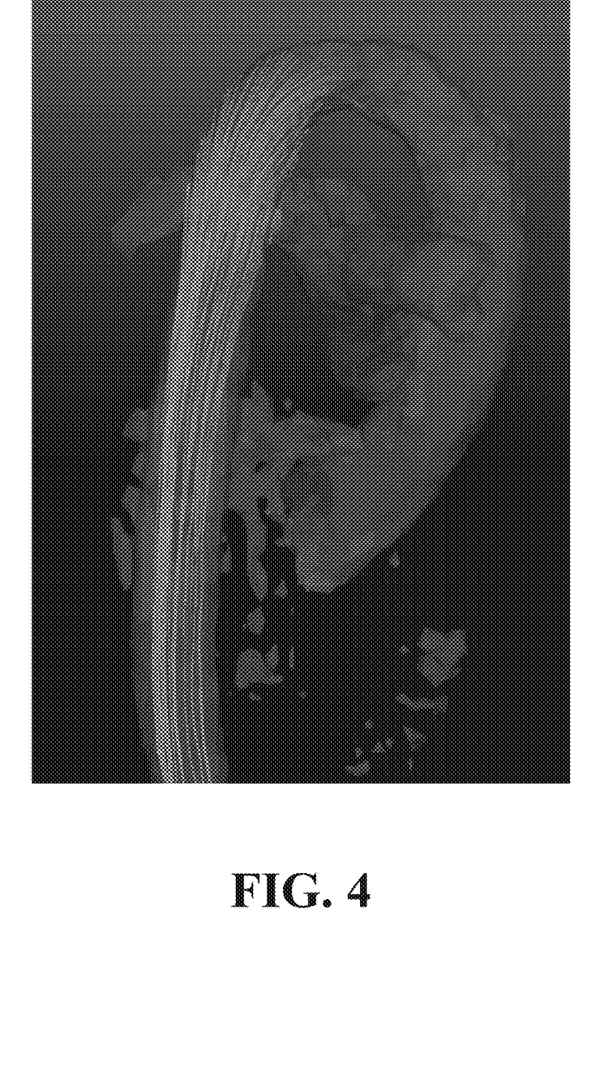
FIG. 4 illustrates an example of an output image according to the method for post-processing flow-sensitive phase contrast magnetic resonance images.

At step 120, the 4D-Flow MRI data is acquired. In one example, the data set comprise four different images for each slice—an anatomical magnitude image and three velocity component images. FIGS. 2a-2b provide examples of anatomical magnitude images and FIGS. 3a-3b provide different examples of velocity component images. The set of image slices, acquired over the total time of the MM scan constitutes the complete 4D-Flow MRI data set. The MRI scanner then transmits the 4D-Flow MRI data set to a computer for post-acquisition processing. The data is acquired, formatted, transmitted, and stored according to standard medical image protocols, known as DICOM. Alternatively, the image data may be acquired in PAR/REC format and converted to the corresponding DICOM format.

Post-acquisition processing may begin with the computer reading the data for each image slice. In one embodiment, as disclosed in step 130, the velocity components and anatomical magnitude for each image slice are isolated. For example, the disclosed method determines the content of each image slice, namely the magnitude and velocity components. This may be accomplished by analyzing the signal histograms for each image throughout all of the image slices and times. The anatomical magnitude image may correspond to the image having the minimum mean, plus or minus a standard deviation, as compared to the other velocity images for a given slice. The anatomical magnitude image from the three velocity component images may then be isolated.

At step 140, each velocity component image can be converted into a physical velocity value. This conversion requires knowledge of the encoding velocity value, $v_{enc}$. Depending on the type of MM scanner and image processing used, the $v_{enc}$ value is either included as a data point in each velocity image, or is known at the time of image acquisition (based on scanning parameters). Additionally, the grayscale value for the images may be identified, which is typically set at about 2048. Of course, the grayscale values may vary and are not particularly limiting. In one embodiment, the following relation is used to convert the velocity component images into corresponding physical velocity values:

$$v_{physical} = \frac{\text{pixel value} - \text{grayscale}}{\text{grayscale}} v_{enc} \quad [1]$$

The pixel value is the data associated with a given physical location on the velocity image. The $v_{physical}$ value for each velocity component image represents a velocity vector for the corresponding image slice. By combining the three orthogonal velocity vectors for the complete set of image slices, the method generates a three-dimensional velocity vector field for the scanned region.

In addition to identifying the velocity vector field for the scanned region, at step 150, the method may also produce a 3D representation (known as an isosurface) of anatomical structures contained in the scanned region. First, the method obtains the anatomical wall of a given structure, such as, for example, a heart chamber or artery, by combining the anatomical magnitude image with the velocity vector field of a given image slice, according to the following relation:

$$\text{Wall} = PV_{anat\ mag}\sqrt{u^2+v^2+w^2} \quad [2]$$

where $PV_{anat\ mag}$ is the pixel value of the anatomical magnitude image and u, v, w are the three components of the velocity vector. Using known mathematical techniques, the method then may calculate an isosurface of Wall to generate a 3D illustration of the anatomical walls contained in the 4D-Flow MRI data set. The mathematical techniques used to calculate an isosurface of Wall are well known in the art.

The method may also provide for the ability to identify Regions of Interest ("ROI") at step 160. In one example, the GUI pictured in FIGS. 2a-2b and FIG. 3a allows the user (e.g. a clinician or an imaging technician) to import the 4D-Flow MRI data set and to view the anatomical magnitude image (as seen in FIGS. 2a-2b) and one of the velocity components (as seen in FIG. 3a).

The method may further provide step 170, where the threshold and velocity parameters are inputted for purposes of isolating and calculating dynamic flow conditions. Flow dynamics quantities may include, but are not limited to, circulation, Reynolds stresses, and helicity. Depending on the user's needs, these flow dynamics quantities may be calculated in planar sections of an image slice, such as, for example, the cross section of a cardiac vessel. Likewise, these flow dynamics quantities may be calculated in volumetric regions or on the surface of the anatomical walls.

Finally, the method may also include step 180, for generating visual representations of fluid flow in 3D anatomical structures by calculating streamlines and pathlines corresponding to the 3D velocity vector field.

Figure 5:
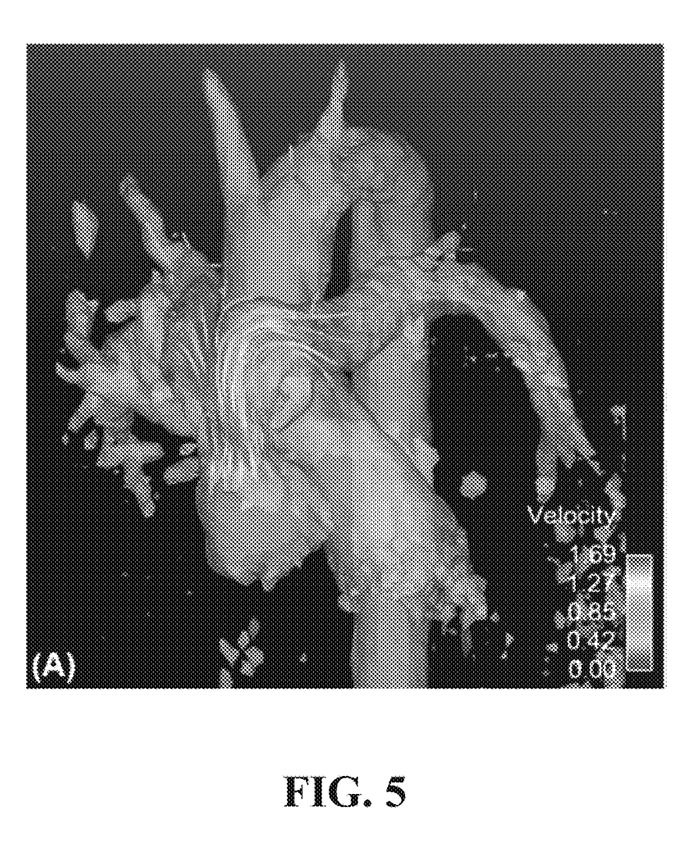
FIG. 5 illustrates an example of an output image generated from a study of the accuracy of a simplified version of Bernoulli's equation in calculating pulmonary transvalvular pressure drops, the study using a method for post-processing flow-sensitive phase contrast magnetic resonance images.
Figure 6:
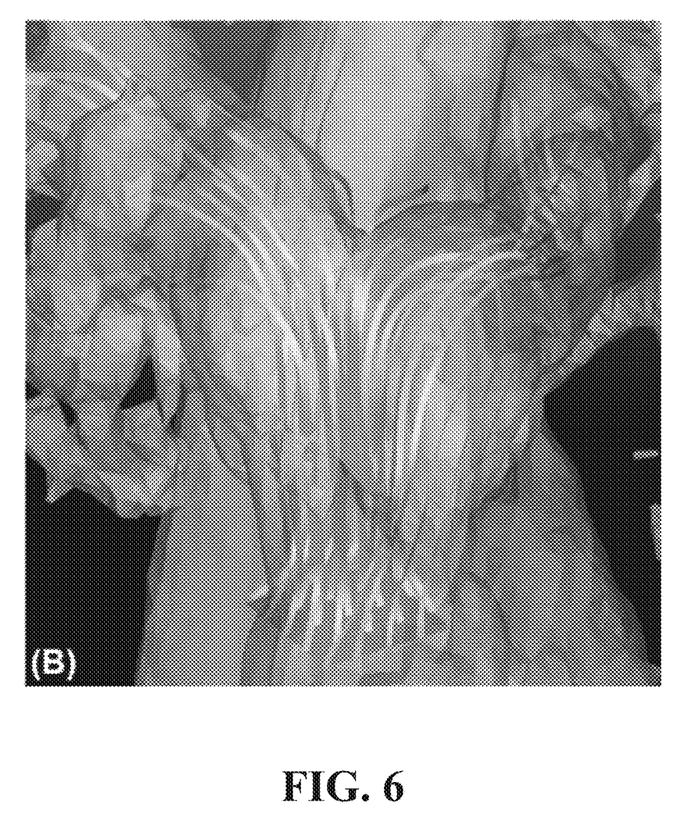
FIG. 6 illustrates another example of an output image generated from a study of the accuracy of a simplified version of Bernoulli's equation in calculating pulmonary transvalvular pressure drops, the study using a method for post-processing flow-sensitive phase contrast magnetic resonance images.

As an example of visual representations of fluid flow in 3D anatomical structures, FIGS. 5 and 6 provide illustrations of a reconstructed velocity field in certain patients. FIG. 5 shows streamlines passing through the pulmonary valve while FIG. 6 illustrates the locations where the streamlines originated. FIGS. 5 and 6 were created as a result of a study to determine the accuracy of a simplified version of Bernoulli's equation in estimating pulmonary transvalvular pressure drop. This study, discussed below, provides an example of one use for the method described above in the flow chart of FIG. 1.

Background of Study

Pulmonary valve stenosis is a common anomaly in patients with congenital heart defects. Quantitative assessment of the severity of pulmonary valve stenosis is mainly based on the transpulmonary pressure drop. Transvalvular pressure drops are commonly estimated by continuous wave Doppler and recently by MRI phase-contrast flow measurements. Cardiac catheterization is the current gold standard for estimation of transvalvular pressure drop; however, this method is not practical on routine follow-up due to its invasive nature. A simplified version of the general Bernoulli's equation is widely used in everyday clinical practice for estimation of maximum transvalvular pressure drop either by echocardiography or MRI. However, maximum transvalvular pressure drop estimated by simplified Bernoulli's equation does not always account for the net transvalvular pressure drop. This is because of the inherent limitation of a simplified Bernoulli equation which fails to account for the unsteady nature of the blood flow through a heart valve and only the peak jet velocity is used in the estimation.

Previously, clinical use of a simplified Bernoulli equation could have been justified since Doppler echocardiography was the only available noninvasive modality. Up until recently, technological limitations did not allow for calculation of velocity changes in time along the flow streamlines. Flow-sensitive MRI data can nowadays provide opportunities to define the unsteady term of the general Bernoulli's equation. This study, investigates the effect of the unsteady term of the Bernoulli equation on the pressure drop through the pulmonary valve in a mixed population of normal subjects and patients with repaired congenital heart defects by post-processing 4D-Flow MRI data similar to a method for post-processing flow-sensitive image data 100 as discussed above.

Methods

Study Subjects:
A total of 20 subjects including 7 patients with repaired tetralogy of Fallot (r-TOF), 7 patients with repaired transposition of great arteries (TGA; Lecompte procedure), 4 patients with repaired (TGA; spiral procedure), and 2 normal volunteers, were enrolled. TABLE 1 below provides more information about these subjects.

TABLE 1

| Group | Sex | Age [years] | Weight [kg] | Reynolds Number | | | |
|---|---|---|---|---|---|---|---|
| | | | | ES | MS | LS | Peak |
| Repaired TOF | M | 11 | 34 | 8,033 | 10,103 | 5,217 | 12,753 |
| | F | 17 | 59 | 12,091 | 14,575 | 12,836 | 17,474 |
| | M | 1 | 10 | 3,892 | 5,963 | 2,898 | 6,791 |
| | F | 22 | 78 | 10,931 | 11,097 | 3,147 | 13,250 |
| | F | 29 | 65 | 2,168 | 2,623 | 1,053 | 2,991 |
| | F | 31 | 55 | 7,370 | 10,103 | 6,542 | 14,492 |
| | M | 58 | 100 | 11,097 | 14,492 | 6,459 | 15,735 |
| Repaired-TGA Lecompte procedure | M | 20 | 65 | 7,702 | 9,441 | 3,064 | 11,511 |
| | M | 22 | 83 | 4,803 | 7,288 | 2,070 | 8,116 |
| | F | 18 | 58 | 3,147 | 3,892 | 2,319 | 4,638 |
| | M | 22 | 75 | 5,052 | 7,702 | 1,905 | 9,524 |
| | M | 22 | 85 | 2,981 | 7,867 | 1,491 | 8,944 |
| | M | 16 | 100 | 3,892 | 5,880 | 2,567 | 7,536 |
| | M | 19 | 70 | 3,809 | 6,459 | 2,402 | 8,033 |
| Repaired TGA spiral procedure | M | 20 | 76 | 3,892 | 6,956 | 2,898 | 8,364 |
| | M | 23 | 81 | 4,223 | 7,039 | 2,070 | 8,861 |
| | M | 20 | 67 | 3,312 | 5,880 | 1,491 | 6,625 |
| | M | 20 | 84 | 5,134 | 11,263 | 1,408 | 13,002 |
| Normal volunteers | F | 23 | 60 | 3,644 | 5,548 | 1,491 | 7,288 |
| | F | 22 | 73 | 4,141 | 5,134 | 1,822 | 6,625 |

ES: Early Systole;
MS: Mid Systole;
LS: Late Systole;
Peak: Peak Systole;
TOF: Tetralogy of Fallot;
TGA: Transposition of Great Arteries.

MR Flow Imaging:

To estimate the pressure drop using different versions of Bernoulli's equation, as described in the following sections, the velocity field in the vicinity of pulmonary valve was quantified in all the studied subjects. This was achieved using 4D PC-MRI in three-dimensional space and time.

Three of the r-TOF patients were studied at Royal Brompton Hospital in London, UK. A 2.9 Tesla Siemens Skyra system (Siemens, Erlangen, Germany) was used, with 26 array elements around the thorax (18-channel flexible anterior coil and 8-channels from a flat spine coil). Acquisitions were ECG-gated, using an RF-spoiled gradient-echo phase contrast sequence with interleaved three-directional velocity encoding to measure flow velocity fields between the right ventricle and proximal pulmonary arteries. Data was acquired with prospective EGG-gating during free-breathing, using a respiratory navigator. The larger dimensions of the acquisition volume were orientated in an oblique sagittal plane so as to include the right ventricle and pulmonary trunk. Echo time was 2.2-2.5 ms, repetition time 4.4-4.8 ms, flip angle 7°, acquired voxel size was 2.1×2.5×2.4 mm, temporal resolution 35-39 ms, by acquisition of 2 raw-data lines per cine frame per cardiac cycle, further accelerated with rate-3 temporal parallel imaging (TGRAPPA). The velocity-encoding range was 1.5-3 m/s, depending on previously determined peaks of velocity through the pulmonary valve.

The rest of the patients and healthy volunteers were studied at University Hospital Kiel in Germany. A 3.0 Tesla Philips scanner (Achieva 3.0T X-series, Philips Medical Systems, Netherlands) was used. Data was acquired with prospective ECG-gating during free-breathing, using a respiratory navigator. Echo time was 1.5-2.0 ms, repetition time 2.5-3.0 ms, flip angle 5°-10°, acquired voxel size was 2.5×2.5×2.5 mm, temporal resolution 35 ms. The velocity-encoding range was 3.0-4.0 m/s in 3 orthogonal directions, TR/TE 4.6/3.2 and FOV 250-350 mm²×100-150 mm. All acquisitions were performed with retrospective ECG-triggering.

Segmentation of the 4D Flow Data:

Software was developed that reads and finds the physical velocity data in space and time from a 4D PC-MRI dataset. In this study, data obtained from Philips and Siemens scanners were saved in two formats: Siemens DICOM and Philips PAR/REG, i.e., Philips data parameters (PAR) and Philips raw reconstructed data (REG), format, respectively.

There were four datasets for each studied subject, consisting of anatomical magnitude and three velocity components image series. 4D-Flow MRI allows detection of the flow dependent phase. The calculation of phase difference images using different velocity-dependent signal phase provides the information needed for computing the velocity images. The pixel values of the velocity image were converted to physical velocity according to the relationship for physical velocity values according to equation [1] discussed above.

Using this software, this velocity field was exported to Ensight (Computational Engineering International, Inc., Apex, NC) for visualization of the walls of the great arteries. This is typically referred to as time-resolved phase contrast angiography (PCMRA) defined according to equation [2] discussed above. As described above, $PV_{anat\ mag}$ is the pixel value of the anatomical magnitude image and u, v, w are the three components of the velocity vector (see FIG. 3). The isosurfaces of PCMRA at peak systole helped identifying the pulmonary trunk as well as the location of the pulmonary valve. Using Ensight and with the help of the isosurfaces of great arteries' wall, the locations of 25 streamlines passing through the pulmonary valve were identified for each time-step during systole. For each subject, the time in systolic phase was normalized with respect to the duration of the systole (over a range from 0 to 1).

Reynolds Numbers:

Reynolds number is a non-dimensional number that indicates the ratio of inertial forces to viscous forces in the flow. It is defined as:

$$Re = \rho VD/\mu$$

where ρ is the density of the fluid (blood), V is the velocity of the flow, D is the diameter of the vessel, and μ is the dynamic viscosity of the blood. High Reynolds number implies that the inertial forces are dominant in the flow and hence viscous forces can be neglected compared to the forces generated by the fluid momentum.

Figure 7:
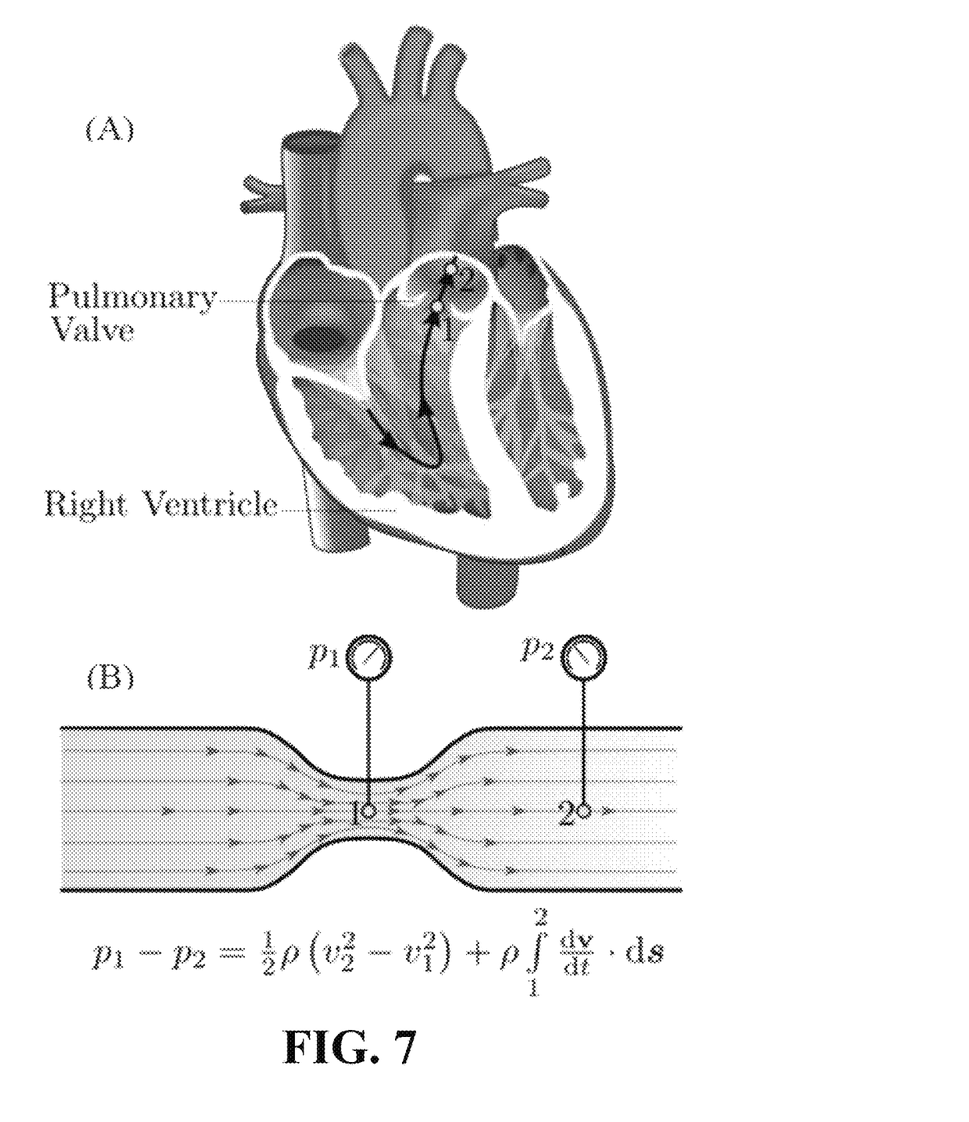
FIG. 7 illustrates the schematic of the streamline passing through the pulmonary valve over which the pressure drop is estimated and the concept of the Bernoulli equation in a simple tube.

Transvalvular Pressure Drop Estimation:

The pressure drop through the pulmonary valve was estimated based on three methods: general Bernoulli's equation, simplified Bernoulli's equation (known as $4V^2$), and modified Bernoulli's equation to be described here. FIG. 7 schematically shows the difference among the estimation methods.

In the general Bernoulli's equation, all the terms of the Bernoulli's equation are included for the estimation of the pressure drop:

$$p_1 - p_2 = \frac{1}{2}\rho(v_2^2 - v_1^2) + \rho \int_1^2 \frac{dv}{dt} ds \quad [3]$$

where $v_2$ and $v_1$ are downstream and upstream velocities, respectively, and the unsteady term consists of the integral of the derivative of velocity with respect to time over a flow streamline between the upstream and downstream velocity points. A flow streamline is an imaginary curve whose tangent at each instant of time represents the direction of the velocity vector of the blood flow. This is the most general equation to estimate the pressure drop with consideration that the viscous effects in the flow is negligible compared to inertial forces. Such flow situations can be identified as flows with a Reynolds number much greater than one.

Simplified Bernoulli's equation, as commonly used in clinics, is a version of Bernoulli's equation that only considers the downstream velocity, $v_2$:

$$p_1 - p_2 = \frac{1}{2}\rho v_2^2 \quad [4]$$

where pressure drop in mmHg equals to $4v_2^2$ if velocity is expressed in cm/s.

Lastly, we describe a modified Bernoulli's equation, where we consider both downstream, $v_2$, and upstream, $v_1$, velocities without considering the effect of the change of velocity with time over the streamline $$\left( \int_1^2 \frac{dv}{dt} \cdot ds \right):$$

$$p_1 - p_2 = \frac{1}{2}\rho(v_2^2 - v_1^2) \quad [5]$$

A code was developed to estimate the pressure drop using the three methods described earlier: through the (1) general Bernoulli, (2) simplified Bernoulli, and (3) modified Bernoulli. The unsteady term of the Bernoulli's equation, i.e., $$\int_1^2 \frac{dv}{dt} \cdot ds$$

was integrated over each streamline. As shown in FIG. 7, point 1 was considered approximately at the level of pulmonary valve and point 2 was considered 1 cm downstream of point 1.

Statistical Analyses:

For the purpose of the statistical analyses, phases of systole (early, middle and late) and position of streamlines within the pulmonary artery lumen were categorized. The systolic phases were grouped into three categories: early (0-30%), middle (30%-60%) and late (60-100%). The position of the streamline was stratified in two regions: interior and boundary streamlines. Interior streamlines were within the inner 50% of the diameter of the pulmonary artery and the streamlines outside this range were labeled as boundary streamlines.

We calculated mean and standard deviation of pressure drop by each method (simplified (i.e. $4V^2$), modified, and general Bernoulli's equations) within each of the six strata formed by systolic phase and position of the streamline; e.g. early-interior, early-boundary, mid-interior, mid-boundary, late-interior, and late-boundary. In addition, we calculated estimates of the regression model for pressure drop as a function of predictors given by methods (simplified, modified, and general Bernoulli's equations), systolic phase (early, mid, late), and streamline's region (interior, boundary). Interactions among the terms were included in the model, including second- and third-order interactions among method, phase and region. In the statistical analyses, the mid-systole, interior region, and the general Bernoulli equation were considered as the reference categories.

A linear mixed effects model was used to fit the model with full account for clustering of observations among the methods, systolic phases and streamlines' regions. Estimates of parameters for the predictors were calculated with 95% confidence intervals. A generalized covariance structure and robust standard errors were also used to guard against model misspecification. An analysis of variance (ANOVA) was calculated for the main effects and interactions. A summary of the variance components (VARCOMP) was calculated for the error terms in the model. These analyses were investigated with and without adjustments for the patient mix.

A two-by-two comparison was also performed between the general and simplified Bernoulli's equations and between the modified and general Bernoulli's equations. Pressure-drop values were analyzed using a linear mixed effect model that involves method, time and their interaction. We implemented a set of six treatment contrasts, given by a set of six specified comparisons among the methods at times within the systole. These comparisons included: simplified Bernoulli's ($4V^2$) versus the general Bernoulli's at early systole, mid systole, and late systole, and modified Bernoulli's versus general Bernoulli's at early systole, mid systole, and late systole.

Results

4D Flow MRI: The three dimensional flow field from the right ventricle through pulmonary valves into the pulmonary artery was obtained for all the studied subjects during systole. As discussed above, FIG. 5 shows the streamlines passing through the pulmonary valve of one of the patients with repaired TGA (Lecompte procedure). The vessel wall shown in the FIGS. 5 and 6 are an approximate representation of the border of the lumen, obtained by equation [2]. The 25 illustrated streamlines in FIGS. 5 and 6 were at the peak systole passing through the pulmonary valve.

Reynolds Number:

to ensure that the inertial forces in the fluid are dominant to the viscous forces and the use of Bernoulli's equation is justified for estimation of pressure drop, Reynolds numbers were calculated for each as described earlier. Reynolds number was calculated during early, middle, end, and peak systole based on the maximum velocity passing through the pulmonary valve. Reynolds numbers were found in the range of 1053 to 17474 for all the studied subjects during the systole as reported in TABLE 1 seen above.

Comparison Among Simplified, Modified and General Bernoulli's Methods:

TABLE 2 below reports the mean response surface over all the principal combinations of the studied parameters. Summaries were taken over all the subjects and repeated measures within the conditions. They were broadly indicative of the effects reported below from the linear models.

TABLE 2

Pressure Drop (mmHg) by Location and Systole Phase within each Method: Reporting Mean ± SD

| Location | Systolic Phase | | |
|---|---|---|---|
| | Early (n = 1,250) | Middle (n = 1,375) | Late (n = 2,250) |
| Method: general Bernoulli's | | | |
| Boundary | 1.12 ± 3.06 | 2.63 ± 4.79 | 0.84 ± 3.15 |
| Interior | 1.37 ± 2.78 | 3.09 ± 5.82 | 1.01 ± 3.06 |
| Method: modified Bernoulli's | | | |
| Boundary | 0.77 ± 2.92 | 2.54 ± 4.80 | 1.11 ± 3.23 |
| Interior | 0.96 ± 2.66 | 2.94 ± 5.78 | 1.36 ± 3.16 |
| Method: simplified Bernoulli's | | | |
| Boundary | 1.57 ± 3.12 | 4.85 ± 6.16 | 2.68 ± 3.93 |
| Interior | 1.67 ± 3.32 | 5.77 = 7.16 | 3.45 ± 4.07 |

Pressure drop was modeled based on three predictors, namely method, systolic phase and the streamline's region. The variance component associated with the region of streamlines was found essentially zero (0.0000) and the third-order interaction of terms was not significant (p=0.05). The model was thus reduced to two predictors, namely methods and systolic phase.

All the main effects and the method/systolic phase interaction were strongly significant in the reduced model as is seen in TABLE 3 seen below:

TABLE 3

Main Inference: Pressure Drop in Method-by-Time Model: ANOVA Table

| | DF | DF | F-value | p-value |
|---|---|---|---|---|
| (Intercept) | 1 | 14559 | 10.24 | 0.0014 |
| Method | 2 | 14559 | 728.74 | 0.0000 |
| Systolic Phase | 2 | 38 | 5.23 | 0.0098 |
| Method: Systolic Phase | 4 | 14559 | 67.67 | 0.0000 |

(method, p-value <0.0001; systolic phase p-value = 0.0098; method/systolic phase, p-value <0.0001)

Figure 8:
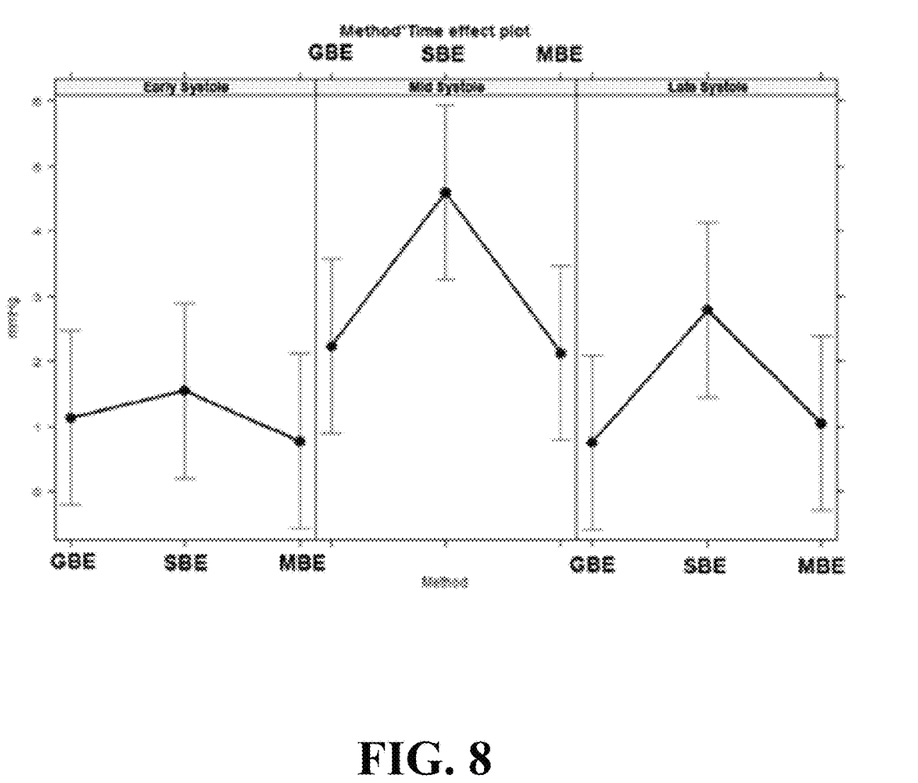
FIG. 8 illustrates a graph showing the estimated mean pressure drop depicted for each combination of method and systolic phase from a study of the accuracy of a simplified version of Bernoulli's equation in calculating pulmonary transvalvular pressure drops, the study using a method for post-processing flow-sensitive phase contrast magnetic resonance images.

The effects are shown in FIG. 8, where the estimated mean pressure drop (mmHg) is depicted for each combination of method and systolic phase.

Exact values for the estimated means and confidence intervals are reported in TABLE 4 below:

TABLE 4

Effects for Pressure Drop Model: Method-by-Time. Comparison of SBE, MBE and GBE Statistical model was defined as Δp~Method * Time

| Method | Time | | |
|---|---|---|---|
| | Early | Mid | Late |
| Method * Time effect | | | |
| GBE | 1.14 | 2.22 | 0.74 |
| SBE | 1.54 | 4.59 | 2.78 |
| MBE | 0.77 | 2.11 | 1.04 |
| Lower 95 Percent Confidence Limits | | | |
| GBE | −0.20 | 0.88 | −0.59 |
| SBE | 0.20 | 3.25 | 1.44 |
| MBE | −0.57 | 0.78 | −0.29 |
| Upper 95 Percent Confidence Limits | | | |
| GBE | 2.48 | 3.56 | 2.08 |
| SBE | 2.88 | 5.93 | 4.12 |
| MBE | 2.11 | 3.46 | 2.38 |

| Variance Components: Estimated Variances | | |
|---|---|---|
| Subject | Time | Within |
| 5.74 | 3.52 | 6.45 |

SBE: Simplified Bernoulli's Equation;
GBE: General Bernoulli's Equation and
MBE: Modified Bernoulli's Equation.

Pressure Drops:

The highest pressure drops were estimated during mid-systole. Simplified Bernoulli's method measured the highest values for pressure drop compared to modified and general Bernoulli's, while measurements by the latter two methods were not appreciably different during peak systole (p=0.27). Phase within the systole affected the comparison among the methods, where the largest difference was observed during mid- and late-systole, and the smallest was found during early-systole.

Subject variation accounted for about 37%, systolic phase about 22% and experimental error about 41% of the total error variance (See TABLE 4 above; variance components for the main inference, where subject, systolic phase and within (i.e., for each patient by fixing the method, time, and location while repeating the estimation) were approximated to be 5.74, 3.52, and 6.45 squared mmHg, respectively).

Two-by-Two Comparisons:

TABLE 5 provided below displays the results of the comparisons between the simplified and general Bernoulli's methods as well as between the modified and the general Bernoulli's methods.

TABLE 5

Comparisons for the Main Inference: Pressure Drop in Method-by-Time Model Comparison of Methods within Systole

| | | Mean difference | SE | 95% Lower | 95% Upper | p-value |
|---|---|---|---|---|---|---|
| SBE vs. GBE | Early | 0.40 | 0.10 | 0.20 | 0.60 | 0.0001 |
| | Mid | 2.36 | 0.10 | 2.17 | 2.55 | 0.0000 |
| | Late | 2.03 | 0.08 | 1.88 | 2.18 | 0.0000 |
| MBE vs. GBE | Early | −0.36 | 0.10 | −0.56 | −0.16 | 0.0003 |
| | Mid | −0.11 | 0.10 | −0.29 | 0.08 | 0.2742 |
| | Late | 0.30 | 0.08 | 0.15 | 0.45 | 0.0001 |

SBE: Simplified Bernoulli's Equation;
GBE: General Bernoulli's Equation and
MBE: Modified Bernoulli's Equation.

This comparison includes the estimated mean difference, standard error, 95% confidence interval (CI) and p-value. The results in TABLE 5 are further discussed in the following two subsections.

Simplified Versus General Bernoulli's Equation:

During the early systole, pressure drop, as measured by simplified Bernoulli's, was on average 0.403 mmHg greater than pressure drop measured by the general Bernoulli's. The difference was found statistically significant with an estimated mean difference of 0.403, 95% CI of [0.204, 0.603] and, p-value of 0.0001. Furthermore, during early systole, the average pressure drop as measured by the general Bernoulli's was found 1.20 mmHg. The relative difference associated with the simplified Bernoulli's method was approximately 25%.

During mid-systole, simplified Bernoulli's on average estimated the pressure drop 2.36 mmHg greater than the ones estimated by the general Bernoulli's. There was a statistically significant difference between the two methods during mid-systole with an estimated mean difference of 2.364, 95% CI of [2.174, 2.554] and p-value<0.0001). This pressure drop was estimated as 2.78 mmHg using the general Bernoulli's. Therefore, the relative difference associated with the simplified Bernoulli's method was approximately 46%.

Lastly, during late systole, pressure drop as estimated by simplified Bernoulli's method was on average 2.033 mmHg greater than pressure drop as estimated by the general Bernoulli's. The difference was found statistically significant with an estimated mean difference of 2.033, 95% CI of [1.885, 2.182] and p-value<0.0001). During late systole, the average pressure drop as measured by the general Bernoulli's was 0.89 mmHg. Hence, the relative difference associated with the simplified Bernoulli's method was approximately 67% during late systole.

Modified Versus General Bernoulli's Equation:

The estimated pressure drop measured by the modified Bernoulli method during early systole was on average 0.364 mmHg less than pressure drop as measured by the general Bernoulli. There was a statistically significant difference between the two methods in the early systole with an estimated mean difference of −0.364, 95% CI of [−0.563, −0.165] and p-value of 0.0003. During early systole, the average pressure drop estimated by the general Bernoulli's was 1.20 mmHg. Thus the relative difference associated with the modified Bernoulli's method was approximately 44% during early systole.

During mid-systole, modified Bernoulli's method on average, estimated the pressure drop 0.106 mmHg less than pressure drop as estimated by the general Bernoulli's. The difference was not found statistically significant with an estimated mean difference of −0.106, 95% CI of [−0.296, 0.084] and p-value of 0.2742). This pressure drop was estimated as 2.78 mmHg using the general Bernoulli's. Therefore, the relative difference associated with the modified Bernoulli's method was approximately 4% during mid-systole.

Finally, during late systole, pressure drop as estimated by the modified Bernoulli's method was on average 0.298 mmHg greater than pressure drop as estimated by the general Bernoulli's. The difference was found statistically significant with an estimated mean difference of 0.298, 95% CI of 0.150, 0.447 and p-value of 0.0001). The average pressure drop as estimated by general Bernoulli's was 0.89 mmHg. Thus the relative difference associated with the modified Bernoulli method was approximately 25% during late systole.

Discussion

The normal size of the pulmonary valve area is about 2.0 cm$^2$ per square meter of body surface area, with no to minimal pressure drop across the valve during systole. In pulmonary valve stenosis, the RV systolic pressure increases, creating a drop across the valve. Potential energy conversion to kinetic energy across the stenotic pulmonary valve results in a high velocity and a pressure drop. Severity of pulmonary stenosis is mainly assessed based on the transpulmonary pressure drop. According to the most recent EAE/ASE guideline, systolic pressure drop derived from the transpulmonary velocity flow curve should be estimated using the simplified Bernoulli's equation. The guideline refers to the work done by Lima et al. in 1983 that validated the simplified Bernoulli's equation in sixteen children with a range of pulmonary valve stenosis from mild to severe using pulsed and continuous-wave Doppler echocardiography. However, that study along with Holen et al. also indicated that the pressure drop estimated by simplified Bernoulli equation does not always predict the pressure drop; for example, they independently showed the pressure drop is underestimated when velocities are low. Alternatively, Yoganathan et al. showed that the simplified Bernoulli's equation reflect the maximal drop, which overestimates the measured drop across a valve or downstream of an obstruction. Overestimation or underestimation of the true pressure drop would misrepresent the conditions under which the flow circulates and consequently affects diagnoses and follow-up.

Simplified version of the Bernoulli's equation only considers a single velocity for pressure drop estimation implying that the entire pressure drop is due to convective acceleration of blood, neglecting losses resulted from inertial acceleration and viscous drag. The Reynolds number, which is the ratio of inertial forces to viscous forces in the flow was in the range of 1053 to 17474 for the studied subjects. As a result, general Bernoulli's equation is a desired estimation for the pressure drop in our studied subjects. While the viscous drag is usually negligible due to high Reynolds number in the vicinity of the transvalvular jet, the simplified Bernoulli's equation for pressure drop estimation can be reasonable only in situations where blood acceleration is minimal such as the particular cases of valvular insufficiency where there is not much change in temporal and spatial blood velocity.

Concerns Regarding Statistical Analyses of the Previous Studies:

The studies discussed above only used simple linear regression that makes a number of assumptions about the predictor variables. For example, the simple linear regression model with standard estimation technique assumes weak exogeneity. This implies the predictor variables are free of error and is not altered by measurement errors, which is not true particularly due to the user-dependency of the ultrasound experiments in those studies. Another assumption for the linear regression is the constancy of the variance that assumes different response variables have identical variance of errors regardless of the values of the predictor variables, which may not be true as the pressure drops (i.e., response variable) can vary over a wide range. The linear regression method also assumes independency of errors that implies the errors of the response variables are not correlated with each other, which may not be true due to the type of experimental conditions both in vivo and in vitro that can result in accumulation of errors.

As a result, a careful statistical study was devised using a linear mixed effects model to fit with full accounting for the clustering of observations among the methods, systolic phases and streamlines' position.

Perspective and Conclusions:

This study confirms that the ratio of inertial to viscous forces (Reynolds number) for transvalvular pulmonary flow is at least 1000. This ratio justifies the use of Bernoulli's equation for estimation of pressure drop as the viscous dissipation is negligible in this flow regimen. Accordingly, the results of this study suggest that overall a statistically significant difference exists between the pressure drops estimated by three different versions of Bernoulli's equation (see TABLEs 2-5). In particular, we found that simplified Bernoulli's method overestimates the pressure drop most among the three during all systolic phases (p<0.0001; see FIG. 9 below). On the other hand, comparison between the modified and general Bernoulli's equations show that the unsteady term is only significant if early and late phases of systole are being considered. This implies that if the mid-systolic period of systole is being considered the modified Bernoulli's equation is likely to be as accurate as general Bernoulli's equations as shown in FIG. 9.

Figure 9:
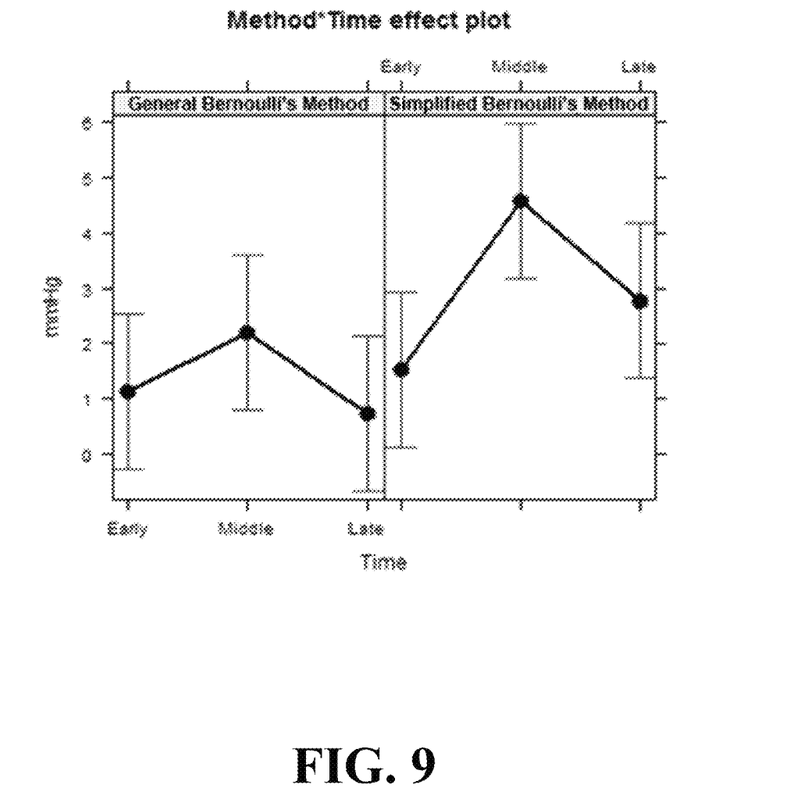
FIG. 9 illustrates a graph showing a comparison of the estimated mean pressure drop between use of the General Bernoulli's Method and a simplified Bernoulli's Method from a study of the accuracy of a Simplified version of Bernoulli's equation in calculating pulmonary transvalvular pressure drops, the study using a method for post-processing flow-sensitive phase contrast magnetic resonance images.

As a result, according to the present study, taking account of both upstream and downstream velocities is likely to be necessary to achieve the best estimation for pressure drop and can even compensate for the effect of the unsteady term, if early and late systolic periods are not the target of the study (see FIG. 9). Additionally, this study suggests that the location of the streamlines—whether they are close to the wall or near the center of the pulmonary artery—does not affect the pressure drop estimation, if the general Bernoulli's equation is used.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention.

What is claimed is:

1. A method for processing flow sensitive data of a region of interest, the method comprising:
   receiving a dataset of 4D flow magnetic resonance imaging (MRI) images corresponding to a scan of the region of interest;
   isolating a velocity component image from the dataset of 4-D flow MRI images;
   converting the velocity component image into a velocity vector field;
   determining at least one fluid dynamic quantity of the region of interest, wherein said at least one fluid dynamic quantity comprises pressure drop, which is estimated by integrating the velocity vector field over streamlines using a form of Bernoulli's equation;
   modeling a location of an anatomical wall within the region of interest;
   generating a visual representation of the anatomical wall and the at least one fluid dynamic quantity; and
   displaying the visual representation.

2. The method of claim 1, wherein the dataset of 4D-Flow magnetic resonance images comprises an anatomical magnitude image and at least one velocity component image.

3. The method of claim 2, where the anatomical magnitude image for a given image slice corresponds to the image of the dataset of 4D-Flow magnetic resonance images having the minimum mean as compared to other velocity component images for the given slice, wherein the mean is an average of first, second and third velocity components for the given image slice contained by the dataset of 4D-Flow magnetic resonance images.

4. The method of claim 1, wherein the dataset of 4D-Flow magnetic resonance images includes a first velocity component image, a second velocity component image, and a third velocity component image.

5. The method of claim 4, wherein each of the first velocity component image, the second velocity component image, and the third velocity component image are converted into a respective first velocity vector field, a respective second velocity vector field, and a respective third velocity vector field.

6. The method of claim 5, further comprising calculating at least one flow dynamics parameter for the region of interest.

7. The method of claim 6, further comprising generating a visual representation of the at least one flow dynamics parameter.

8. The method of claim 7, further comprising displaying the visual representation of the anatomical wall.

9. The method of claim 6, wherein the at least one flow dynamics parameter comprises circulation.

10. The method of claim 6, wherein the at least one flow dynamics parameter comprises Reynold stresses.

11. The method of claim 6, wherein the at least one flow dynamics parameter comprises helicity.

12. The method of claim 11, wherein scanning further comprises saving the data into PAR/REC format or DICOM format.

13. The method of claim 11, further comprising selecting a region of interest using a graphic user interface.

14. The method according to claim 11, wherein said form of Bernoulli's equation is:

$$p_1 - p_2 = \frac{1}{2}\rho(v_2^2 - v_1^2) + \rho\int_1^2 \frac{dv}{dt} ds$$

where $p_1$ and $p_2$ are upstream and downstream pressures, respectively, $\rho$ is the density of a fluid in the region of interest, $v_1$ and $v_2$ are upstream and downstream velocities, respectively, and wherein an unsteady term consists of the integral of the derivative of velocity with respect to time over a flow streamline between the upstream and downstream velocity points.

15. A method for generating fluid flow images of a region of interest, the method comprising:
   receiving a dataset of 4D flow magnetic resonance images from a scan of the region of interest, wherein the dataset comprises an anatomical magnitude image, a first velocity component image, a second velocity component image, and a third velocity component image;

isolating the anatomical magnitude image, the first velocity component image, the second velocity component image, and the third velocity component image from the dataset of 4D-flow magnetic resonance images;

converting the first, second, and third velocity component images into a velocity vector field;

modeling a location of an anatomical wall within the region of interest;

calculating at least one fluid dynamics parameter for the region of interest, wherein said at least one fluid dynamics parameter comprises pressure drop, which is estimated by integrating the velocity field over streamlines using a form of Bernoulli's equation;

generating a visual representation of the anatomical wall and the at least one fluid dynamics parameter; and displaying the visual representation.

16. A method to generate fluid flow images of a region of interest using magnetic resonance images, the method comprising:

receiving a plurality of 4D-Flow magnetic resonance image sets from a scan of the region of interest, wherein each image set comprises an anatomical magnitude image, a first velocity component image, a second velocity component image, and a third velocity component image;

converting the first, second, and third velocity component images into a first, second, and third physical velocity data set for each of the plurality of 4D-Flow magnetic resonance image sets;

modeling a location of an anatomical wall within the region of interest, wherein the location of the anatomical wall is based on the mathematical combination of the anatomical magnitude image and the first, second, and third physical velocity data sets for each of the plurality of 4D-Flow magnetic resonance image sets;

calculating at least one fluid dynamics parameter for the region of interest, wherein said at least one fluid dynamics parameter comprises pressure drop, which is estimated by integrating the physical velocity data sets over streamlines using a form of Bernoulli's equation;

generating a visual representation of the anatomical wall and the at least one fluid dynamics parameter; and displaying the visual representation.

* * * * *

UNITED STATES PATENT AND TRADEMARK OFFICE
CERTIFICATE OF CORRECTION

PATENT NO. : 10,134,127 B2  
APPLICATION NO. : 15/102853  
DATED : November 20, 2018  
INVENTOR(S) : Ahmad Falahatpisheh Page 1 of 1

It is certified that error appears in the above-identified patent and that said Letters Patent is hereby corrected as shown below:

Column 2, Line 28, change "wall" to --wall.--.

Column 3, Line 62, change "images;" to --images.--.

Column 11, Line 36 (approx.), change "5.77 = 7.16" to --5.77±7.16--.

Column 15, Line 56, in Claim 1, change "4D flow" to --4D-Flow--.

Column 15, Line 60, in Claim 1, change "4-D flow" to --4D-Flow--.

Column 16, Line 13 (approx.), in Claim 3, change "mean" to --mean,--.

Column 16, Line 42 (approx.), in Claim 12, change "claim 11," to --claim 1,--.

Column 16, Line 44 (approx.), in Claim 13, change "claim 11," to --claim 1,--.

Column 16, Line 46 (approx.), in Claim 14, change "claim 11," to --claim 1,--.

Column 16, Line 55, in Claim 14, change "p" to --ρ--.

Column 16, Line 63, in Claim 15, change "4D flow" to --4D-Flow--.

Column 17, Line 4, in Claim 15, change "4D-flow" to --4D-Flow--.

Signed and Sealed this  
Eleventh Day of June, 2019

Andrei Iancu  
*Director of the United States Patent and Trademark Office*